United States Patent [19]

Abou-Gharbia et al.

[11] Patent Number: 4,921,958
[45] Date of Patent: May 1, 1990

[54] PIPERAZINYLALKYLCARBOXYLIC ACID ADAMANTYLAMIDES

[75] Inventors: Magid A. Abou-Gharbia, Glen Mills; John P. Yardley, Gulph Mills; Wayne E. Childers, Jr., Yardley, all of Pa.; Ian A. Cliffe, Slough, England

[73] Assignees: American Home Products Corporation, New York, N.Y.; John Wyeth & Brother Limited, Maidenhead, England

[21] Appl. No.: 413,407

[22] Filed: Sep. 27, 1989

Related U.S. Application Data

[63] Continuation-in-part of Ser. No. 297,509, Jan. 13, 1989, abandoned.

[30] Foreign Application Priority Data

Apr. 22, 1989 [GB] United Kingdom ............... 8909209

[51] Int. Cl.$^5$ .................. C07D 403/04; C07D 295/10; C07D 295/12
[52] U.S. Cl. .................................... 544/295; 544/357; 544/360; 544/380
[58] Field of Search ............... 544/295, 380, 360, 357

[56] References Cited

U.S. PATENT DOCUMENTS 4,202,898 5/1980 Depoortere ................ 424/250

FOREIGN PATENT DOCUMENTS 7017031 5/1971 Netherlands .

OTHER PUBLICATIONS

Derwent Abstract 85000957/01–German Patent No. 3321-969 (1984).
Derwent Abstract 87-049798/07–U.S. Pat. No. 4,640,921 (1987).
Barone, et al., Drug Clin. Pharm., 20, 770, 1986.

Primary Examiner—John M. Ford
Attorney, Agent, or Firm—R. K. Jackson

[57] ABSTRACT

The compounds of the formula:

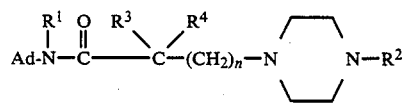

wherein Ad is 1-adamantyl, 2-adamantyl or 3-noradamantyl; n is 1,2,3,4 or 5; $R^1$ hydrogen, alkyl, phenyl, benzyl, or substituted phenyl or benzyl in which the substituent is alkyl, alkoxy, halo, cyano, nitro or trifluoromethyl; $R^2$ is phenyl, benzyl or substituted phenyl or benzyl in which the substituent is alkyl, alkoxy, halo, nitro, cyano or perhalomethyl, 2-, 3-, or 4-pyridinyl, 2-, 4- or 5-pyrimidinyl or 2- or 3-pyrazinyl; $R^3$ and $R^4$ are, independently, hydrogen, methyl, phenyl or benzyl; or a pharmaceutically acceptable salt thereof, are useful anxiolytic/antidepressant agents, with elements of antipsychotic activity.

5 Claims, No Drawings

PIPERAZINYLALKYLCARBOXYLIC ACID ADAMANTYLAMIDES

RELATED APPLICATION

U.S. Patent Application No. 07/197,890, filed May 24, 1988 by Magid A. Abou-Gharbia and John P. Yardley, discloses certain reverse amides of the compounds of this application. The reverse amides possess antipsychotic and anxiolytic activity.

This application is a continuation-in-part of U.S. Patent application Ser. No. 07/297,509, filed Jan. 13, 1989 by Magid A. Abou-Gharbia, John P. Yardley and Wayne E. Childers, Jr., entitled Piperazinylalkylcarboxylic Acid Adamantylamides.

BACKGROUND OF THE INVENTION

Derwent Abstract 85-000957/01 of German Application 3,321,969 discloses 1-pyrimidyl-4-substituted piperazine derivatives which possess a broad variety of CNS activity including anxiolytic and antidepressant properties. Netherlands Patent 7,017,031 discloses 8-(heteroarylpiperazinylalkyl)-8-azaspiro[4,5]decane-7,9-diones as tranquilizers. U.S. Pat. No. 4,640,921 (Derwent Abstract 87-049798/07) discloses the use of the buspirones of the Netherlands patent in the treatment of sexual dysfunction in anxious patients. The anxiolytic activity of buspirone-like compounds has been attributed to their selective activity at a serotonin (5-hydroxytryptamine; 5-HT) subtype receptor designated the 5-HT$_{1A}$ receptor. U.S. Pat. No. 4,202,898 discloses the treatment of anxiety and depression with aromatically substituted piperazine derivatives, 5-HT$_2$ antagonists, such as Ritanserin, lack 5-HT$_{1A}$ affinity but demonstrate clinical efficacy as anxiolytic-antidepressant agents (Barone et al., Drug Clin. Pharm., 20, 770, 1986).

DESCRIPTION OF THE INVENTION

In accordance with this invention there is provided a group of novel compounds, some of which exhibit selective serotonin 5HT$_{1A}$ receptor affinity which characterizes them as antidepressants and anxiolytics and some of which exhibit both 5HT$_{1A}$ receptor affinity and dopamine D2 receptor binding which characterizes them as anxiolytic/antidepressant agents with elements of antipsychotic activity. The compounds of this invention are of the following structural formula:

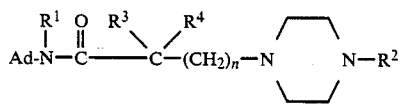

wherein
Ad is 1-adamantyl, 2-adamantyl, or 3-noradamantyl;
n is 1, 2, 3, 4 or 5;
R$^1$ is hydrogen, alkyl of 1 to 3 carbon atoms, phenyl, benzyl, or substituted phenyl or benzyl in which the substituent is alkyl of 1 to 3 carbon atoms, alkoxy of 1 to 3 carbon atoms, halo, cyano, nitro or trifluoromethyl;
R$^2$ is phenyl, benzyl or substituted phenyl or benzyl in which the substituent is alkyl of 1 to 3 carbon atoms, alkoxy of 1 to 3 carbon atoms, halo, nitro, cyano or perhalomethyl, 2-, 3-, or 4-pyridinyl, 2-, 4- or 5-pyrimidinyl or 2- or 3-pyrazinyl; and R$^3$ and R$^4$ are, independently, hydrogen, methyl, phenyl or benzyl;
or a pharmaceutically acceptable salt thereof.

The pharmaceutically acceptable salts are conveniently derived by conventional means from such acids as hydrochloric, hydrobromic, sulfuric, phosphoric, methane sulfonic, nitric, p-toluene sulfonic, acetic, citric, maleic, succinic acid, and the like. The halogens embraced by the term halo are chlorine, bromine, iodine and fluorine, preferably chlorine, bromine or fluorine. The preferred compounds are those derived from 1-adamantanamine.

The compounds of this invention may be prepared by a variety of synthetic routes using conventional methods. For instance, noradamantan-3-amine or 1- or 2-adamantanamine may be conveniently reacted with the appropriately substituted

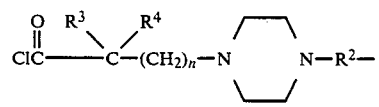

in CH$_2$Cl$_2$ or CHCL$_3$ and in the presence of an acid acceptor such as triethylamine. Alternatively, the carboxylic acids

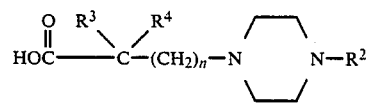

may be reacted with noradamantan-3-amine or 1- or 2-adamantanamine in the presence of a coupling agent conventionally used to produce amides, such as dicyclohexylcarbodiimide and preferably 1,1'-carbonyldiimidazole, iso-butylchloroformate or diphenylphosphinyl chloride. Similarly, the reactant

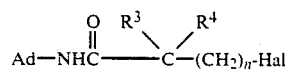

may be employed to alkylate the amine

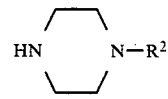

conventionally.

The following examples illustrate, without limitation, the specific methods employed in production of a representative number of compounds embraced by this invention.

EXAMPLE 1

4-(2-pyrimidyl)-N-tricyclo[3.3.1.1(3.7)]dec-1-yl-1-piperazinepropanamide

To a suspension of 4-(2-pyrimidinyl)-1-piperazine hydrochloride (4.56 gm, 0.019 mol) in 150 ml of dry dimethylformamide was added diisopropylethylamine (7.62 gm, 0.06 mol) and 3-bromo-N-tricyclo[3.3.1.1(3,7)]dec-1-ylpropanamide hydrochloride (5.51 gm, 0.019 mol). The stirred mixture was at 38° C. for 18 hours, and then a 54° C. for an additional 24 hours. The reaction mixture was then concentrated on a rotary evaporator, diluted with methylene chloride, washed with three portions of water, dried over anhydrous magnesium sulfate, and concentrated on a rotary evaporator. The desired product (TLC on silica gel using a 10% methanol in ethyl acetate solvent system, Rf=0.3) was isolated by preparative high pressure liquid chromatography (HPLC) on silica gel (using a gradient consisting of from 10% ethyl acetate in hexane to 10% methanol in ethyl acetate) and converted to the trihydrochloride salt (0.7 gm, 8%), m.p.=273°–275° C.

Elemental Analysis for $C_{21}H_{31}N_5O.3H_2O$
Calc'd: C, 52.67; H, 7.16; N, 14.63
Found: C, 52.46; H, 6.89; N, 14.54

EXAMPLE 2

4-(2-methoxyphenyl)-N-tricyclo[3.3.1.1(3,7)]dec-1-yl-1-piperazinepropanamide To a suspension of 4-(2-methoxyphenyl)-1-piperazine (0.67 gm, 0.0035 mol) in 50 ml of methylene chloride was added diisopropylethylamine (0.49 gm, 0.0038 mol) and 3-bromo-N-tricyclo[3.3.1.1(3,7)]dec-1-yl propanamide (0.98 gm, 0.0034 mol). The resulting mixture was stirred at room temperature for three days. The reaction mixture was then washed with two portions of water, dried over anhydrous sodium sulfate, and concentrated on a rotary evaporator. The desired product (TLC on silica gel using a 10% methanol in ethyl acetate solvent system, Rf=0.45) was isolated by preparative high pressure liquid chromatography on silica gel (using a solvent gradient consisting of from ethyl acetate to 4% methanol in dry acetate) and converted to the dihydrochloride salt (0.33 gm, 20%), m.p.=232°–234° C.

Elemental Analysis for $C_{24}H_{35}N_3O_2.2HCL.\frac{1}{2}H_2O$
Calc'd: C, 60.12; H, 7.99; N, 8.76
Found: C, 60.45; H, 8.11; N, 8.79

EXAMPLE 3

N-(1-Tricyclo[3.3.1.1(3,7)]decyl)-3-[1-[4-(2-methoxyphenyl)piperazinyl]]-2-phenylpropanamide 1-(2-Methoxyphenyl)piperazine (22.6 g, 0.118 mol) and atropic acid (174 g, 0.118 mol) in ethanol (300 ml) were heated under reflux for 18 hours, cooled to room temperature, and evaporated in vacuo. The solid was triturated with acetone (3×100 ml) to give a first crop of α-[1-[4-(2-methoxyphenyl)piperazinyl]methyl]phenyl acetic acid (13.8 g) as white crystals. The filtrate was evaporated in vacuo to give an oil which slowly crystallized over a one month period of time. The solid was triturated with acetone (200 ml) to give a second crop of the hemihydrate of the α-[1-[4-(2-methoxyphenyl)piperazinyl]methyl]phenylacetic acid (9.01 g) as white crystals, m.p. 160°–163° C.

Elemental Analysis for $C_{20}H_{24}N_2O_3.0.5H_2O$
Calc'd: C, 68.8; H, 7.2; N, 8.0
Found: C, 68.4; H, 7.2; N, 7.9

A stirred suspension of N-methylmorpholine (0.61 ml, 5.6 mmol) and the product of the preceding paragraph (1.894 g, 5.6 mmol) in dimethylformamide (10 ml) at −15° C. was treated with isobutyl chloroformate (0.73 ml, 5.6 mmol). After 5 minutes, 1-adamantylamine (0.885 g, 5.85 mmol) was added and the suspension warmed to room temperature. After 1 hour, the viscous suspension was diluted with dimethylformamide (10 ml). After 72 hours, the mixture was poured into water (200 ml) and extracted with chloroform (2×200 ml). The extracts were washed with brine (100 ml), dried (MgSO4), and evaporated in vacuo. The residue was purified by chromatography (silica; diethyl ether) to give the title compound as a foam.

The dihydrochloride salt of the product was prepared from methanol-diethyl ether with ethereal hydrogen chloride as white crystals (0.392 g), m.p. 244°–246° C. (dec.).

Elemental Analysis for $C_{30}H_{39}N_3O_2.2HCl$
Calc'd: C, 65.9; H, 7.6; N, 7.7
Found: C, 65.7; H, 7.7; N, 7.6

The compounds of this invention are antidepressant, anxiolytic agents useful in the treatment of depression and/or anxiety as a singular, primary mental problem as well as secondary, attending problems such as sexual dysfunction. Some of the compounds possess sufficient dopaminergic activity to be useful in treating psychoses such as schizophrenia or paranoia. Examples of compounds with sufficient limbic $D_2$ (dopamine) receptor affinity to be considered to have an antipsychotic parameter are those of Example 2 which exhibited 74 percent inhibition of $^3$H-spiroperidol binding to limbic brain tissue at 1 μM concentration of the test compound. The $D_2$ receptor affinity of the compounds of this invention was determined by a modification of the test procedure of Fields et al., Brain Res. 136, 578 (1977) and Yamamura et. al., eds., Neurotransmitter Receptor Binding, Raven Press, N.Y. (1978) as discussed in U.S. No. 4,636,563. The percentage reduction of $^3$H-spiroperidol binding at 1 μM concentration of test compound is reported, infra.

The serotoninergic properties of the compounds of this invention were established by the procedure of Hall et al., J. Neurochem. 44, 1685–1696 (1985) by demonstrating that representative compounds exemplified herein displace $^3$H-8-OH DPAT (dipropylaminotetralin) from the 5-HT$_{1A}$ serotonin receptor subtype. The results of this standard pharmacological procedure are reported, infra, as the percent inhibition at 1 μM concentration of test compound and by providing the inhibition constant Ki for the specific test compound where that calculation has been made from appropriate IC$_{50}$ values. Buspirone exhibits a Ki value of 10 nM (97% inhibition at 1 μM) in this test procedure.

| Affinity for 5-HT$_{1A}$ Receptor Sites | | |
|---|---|---|
| Compounds of Example | % Inhibition at 1 μM (Ki in nM) | % Inhibition at 100 nM |
| 1 | 79% (130 nM) | |
| 2 | 100% ( 9 nM) | 86% |
| 3 | ( 83 nM) | |

| Affinity for D$_2$ Receptor Sites | |
|---|---|
| Compound of Example | % Inhibition at 1 μM |
| 1 | 14% |
| 2 | 74% |

In qualitatively evaluating the above data, high affinity values for 5-HT$_{1A}$ receptors correlate (by analogy with buspirone) with anxiolytic-antidepressant activity, while lower values reflect a lesser activity. High affinity values for D$_2$ receptor binding begin to show some antipsychotic activity.

Hence, the compounds of this invention are antidepressant/anxiolytic agents useful in the treatment of depression and in alleviating anxiety and in the case of the product of Example 2 and analogously substituted phenyl containing compounds, they have some meaningful antipsychotic activity which is useful in the treatment of psychoses such as paranoia and schizophrenia. As such, the compounds of this invention may be administered to a patient in need thereof, either neat or with a conventional pharmaceutical carrier. The pharmaceutical carrier may be solid or liquid as suitable for oral or parenteral administration.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is subdivided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of anxiety, depression, psychoses, etc. must be subjectively determined by the attending physician. The variables involved include the specific state of depression, anxiety or psychoses and the size, age and response pattern of the patient.

What is claimed is:

1. A compound of the formula:

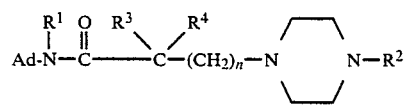

wherein
  Ad is 1-adamantyl, 2-adamantyl or 3-noradamantyl;
  n is 1, 2, 3, 4, or 5;
  $R^1$ is hydrogen, alkyl of 1 to 3 carbon atoms, phenyl, benzyl, or substituted phenyl or benzyl in which the substituent is alkyl of 1 to 3 carbon atoms, alkoxy of 1 to 3 carbon atoms, halo, cyano, nitro or trifluoromethyl;
  $R^2$ is phenyl, benzyl or substituted phenyl or benzyl in which the substituent is alkyl of 1 to 3 carbon atoms, alkoxy of 1 to 3 carbon atoms, halo, nitro, cyano or perhalomethyl, 2-, 3- or 4-pyridinyl, 2-, 4- or 5-pyrimidinyl or 2- or 3-pyrazinyl;
and
  $R^3$ and $R^4$ are, independently, hydrogen, methyl, phenyl or benzyl; or a pharmaceutically acceptable salt thereof.

2. The compound of claim 1 in which Ad is 1-adamantyl.

3. The compound of claim 1 which is 4-(2-pyrimidyl)-N-tricyclo[3.3.1.1(3,7)]dec-1-yl-1-piperazinepropanamide, or a pharmaceutically acceptable salt thereof.

4. The compound of claim 1 which is 4-(2-methoxyphenyl)-N-tricyclo[3.3.1.1(3,7)]dec-1-yl-piperazinepropanamide, or a pharmaceutically acceptable salt thereof.

5. The compound of claim 1 which is N-(1-tricyclo[3.3.1.1(3,7)]decyl)-3-[1-[4-(2-methoxyphenyl)-piperazinyl]]-2-phenylpropanamide.

* * * * *